(12) United States Patent
Park

(10) Patent No.: US 8,971,995 B2
(45) Date of Patent: Mar. 3, 2015

(54) BLOOD VESSEL SIZING DEVICE

(75) Inventor: Richard B. Park, St. Charles, IL (US)

(73) Assignee: Sizer LLC, St. Charles, IL (US)

(*) Notice: Subject to any disclaimer, the term of this patent is extended or adjusted under 35 U.S.C. 154(b) by 53 days.

(21) Appl. No.: 13/427,084

(22) Filed: Mar. 22, 2012

(65) Prior Publication Data

US 2013/0253301 A1 Sep. 26, 2013

(51) Int. Cl.
*A61B 5/05* (2006.01)

(52) U.S. Cl.
USPC .......................... 600/426; 600/407; 378/163

(58) Field of Classification Search
USPC ........................ 600/407–430; 378/162–165
See application file for complete search history.

(56) References Cited

U.S. PATENT DOCUMENTS

| | | | |
|---|---|---|---|
| 3,812,842 A | 5/1974 | Rodriguez | |
| 4,506,676 A | 3/1985 | Duska | |
| 5,193,106 A | 3/1993 | DeSena | |
| 5,216,700 A | 6/1993 | Cherian | |
| 5,970,119 A | 10/1999 | Hofmann | |
| 6,084,941 A | 7/2000 | Stenstrom | |
| 6,333,970 B1 | 12/2001 | LeMaitre et al. | |
| 6,356,621 B1 | 3/2002 | Furumori et al. | |
| 7,127,826 B2 * | 10/2006 | Russell | 33/758 |
| 7,876,884 B2 | 1/2011 | Davis | |
| 7,978,825 B2 | 7/2011 | Ngo | |
| 2005/0000133 A1 * | 1/2005 | Russell | 40/630 |
| 2007/0163139 A1 * | 7/2007 | Russell | 33/758 |
| 2007/0280406 A1 | 12/2007 | Geliebter | |
| 2009/0022272 A1 | 1/2009 | Joseph et al. | |
| 2009/0253981 A1 | 10/2009 | Hamilton et al. | |
| 2012/0059244 A1 | 3/2012 | McClelland et al. | |
| 2012/0302863 A1 * | 11/2012 | O'Neill | 600/407 |

OTHER PUBLICATIONS

International Search Report and Written Opinion issued Jun. 14, 2013 for related Intl. Appln. No. PCT/US2013/033154.

* cited by examiner

*Primary Examiner* — Sanjay Cattungal
(74) *Attorney, Agent, or Firm* — Banner & Witcoff, Ltd.

(57) ABSTRACT

Medical devices and methods for determining the size of blood vessels are disclosed. In an embodiment, a blood vessel sizing device includes a marker configured for placement on the skin of a patient. The marker defines a substantially circular shape and includes a plurality of radiopaque substantially concentric circles. In an embodiment, a blood vessel sizing method includes placing a marker having a plurality of substantially concentric circles on the skin of a patient, imaging a blood vessel of the patient and the marker, and comparing the imaged blood vessel to the imaged circles to determine the blood vessel size.

16 Claims, 2 Drawing Sheets

BLOOD VESSEL SIZING DEVICE

BACKGROUND

The present disclosure relates generally to medical devices and more specifically to medical devices for determining or measuring blood vessel size during, for example, an angiogram.

Determining blood vessel size quickly and accurately is important, for example, when treating stenotic vessel with angioplasty or stent. If blood vessel size is incorrectly determined, a stent that is too large for the actual blood vessel size could be selected. Using an oversized stent can damage, dissect or even perforate the blood vessel.

Diagnostic imaging using, for example, X-ray machines, computer tomography machines or magnetic resonance imaging machines, generate images of blood vessels including any narrowing of blood vessels. A clinician uses these images to determine blood vessel size and stenosis. But using such images has inherent limitations. For example, computer tomography imaging accuracy can be affected by sampling, size of display field of view and/or intravascular density of a contrast material. During emergency procedures, computer tomography or magnetic resonance imaging measurements may not be available.

A need accordingly exists for medical devices and methods that improve the process of determining blood vessel size during, for example, angiographic procedures.

SUMMARY

The present disclosure is directed to medical devices and methods for determining blood vessel sizes based upon, for example, angiographic images of the vessels. Such blood vessel images can be generated, for example, via angiograms. In an embodiment, a blood vessel sizing device includes a marker configured placement on the skin of a patient near a blood vessel to be imaged. The marker defines a substantially circular shape and includes a plurality of radiopaque or radiodense at least substantially concentric circles. When a computer machine generates an angiographic image of the blood vessel, the radiopaque circles cause the circles to be visible on the generated image (along with the blood vessel image). A clinician can quickly and accurately determine the actual size of the blood vessel size by comparing the blood vessel image to the image of the concentric circles, which have a known or illustrated dimension.

In an embodiment, the marker is adhesive so that a user can easily secure or place the marker onto the skin of a patient. In various embodiments, the marker includes a plurality of different radiopaque or radiodense symbols such as numbers or geometric shapes that are also visible on the machine generated image. The symbols each represent a diameter of one of the plurality of substantially concentric circle, which enables a user to quickly and accurately determine the actual size of the blood vessel based upon the generated image. In one embodiment, the radiopaque circles range from about 2 mm to about 20 mm in diameter. In various embodiments, the marker includes four substantially concentric radiopaque circles having diameters of 4 mm, 6 mm, 8 mm and 10 mm. In alternative embodiments, the four substantially concentric radiopaque circles have diameters of 14 mm, 16 mm, 18 mm and 20 mm.

In another embodiment, a blood vessel sizing method includes placing a marker having a plurality of radiopaque substantially concentric circles on the skin of a patient, generating an image of the patient's blood vessel and the circles, and then comparing the image of the blood vessel to the image of at least one of the concentric circles to determine the actual size of the blood vessel. The image can be generated using, for example, an angiogram.

The actual size of the blood vessel is determined by measuring a diameter of the imaged blood vessel and comparing the measured diameter to at least one of the images of plurality of radiopaque substantially concentric circles. A mechanical instrument (e.g., calipers) can be used in an embodiment to measure the diameter of the imaged blood vessel and compare it to the plurality of radiopaque circles.

It is accordingly an advantage of the present disclosure to provide a medical device that simplifies and improves blood vessel size determination.

It is a further advantage of the present disclosure to provide a method for improving the process for blood vessel size determination.

Additional features and advantages are described herein, and will be apparent from the following Detailed Description and the figures.

DETAILED DESCRIPTION

The present disclosure is directed to medical devices and methods for determining blood vessel size based upon machine generated images of the blood vessel. Such images can be generated, for example, via an angiogram.

Figure 1:
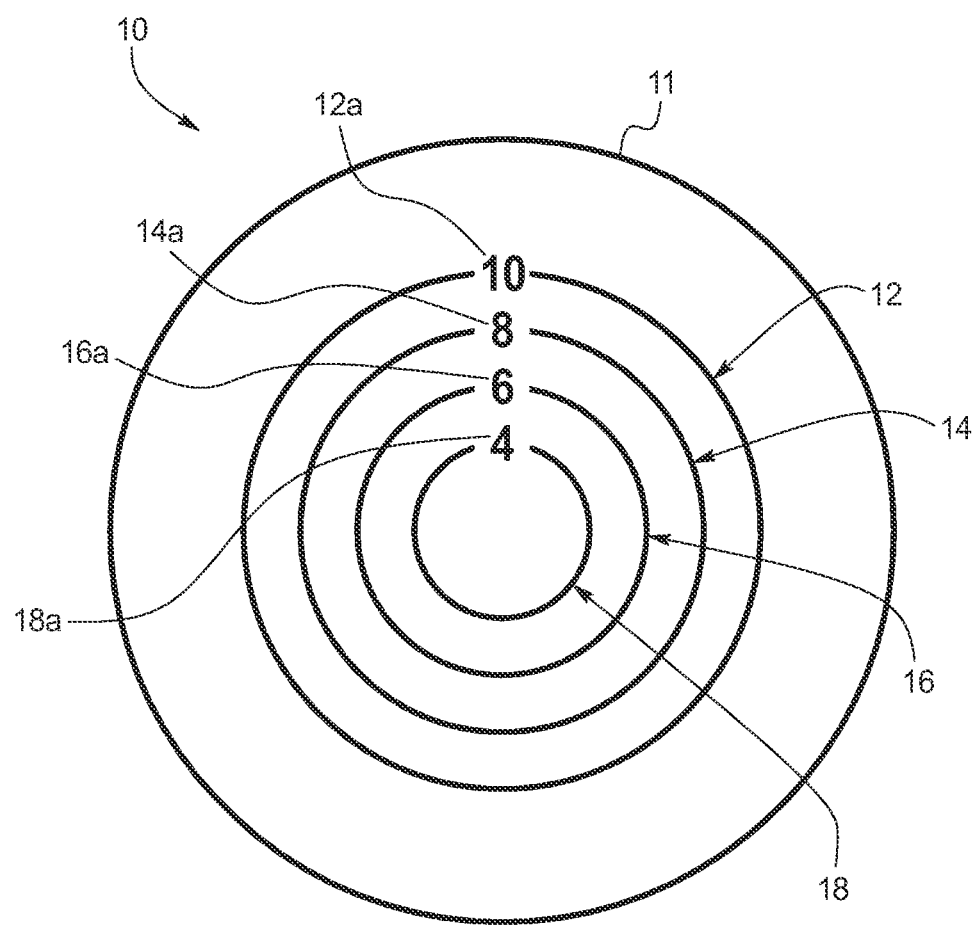
FIG. 1 is a top view of a medical device of the present disclosure illustrating a marker having a plurality of radiopaque substantially concentric circles.

FIG. 1 illustrates an embodiment of a medical device 10 of the present disclosure, which includes a marker 11 defining a substantially circular shape. Marker 11 is configured to be placed on the skin of a patient and has a plurality of radiopaque substantially concentric circles 12, 14, 16, 18. In an embodiment, a surface of marker 11 includes an adhesive that enables maker 11 to be quickly and easily stuck to or secured to the patient's skin. Marker 11 has an outside diameter that is larger than the diameter of outermost radiopaque concentric circle 18. Marker 11 also includes radiopaque symbols 12a, 14a, 16a and 18a, each of which represents a corresponding diameter of concentric circles 12, 14, 16 and 18. For example, FIG. 1 illustrates four radiopaque numerical symbols of 10 mm, 8 mm, 6 mm and 4 mm, which represent the diameters of concentric circles 12, 14, 16 and 18, respectively. It should be appreciated that symbols 12a, 14a, 16a, 18a can be any suitable symbols representing the diameter of concentric circles 12, 14, 16 and 18. In an embodiment, the symbols are a plurality of different geometric shapes, such as triangles, circles, squares and pentagons, each representing the diameter of one of the circles 12, 14, 16 and 18.

Figure 2:
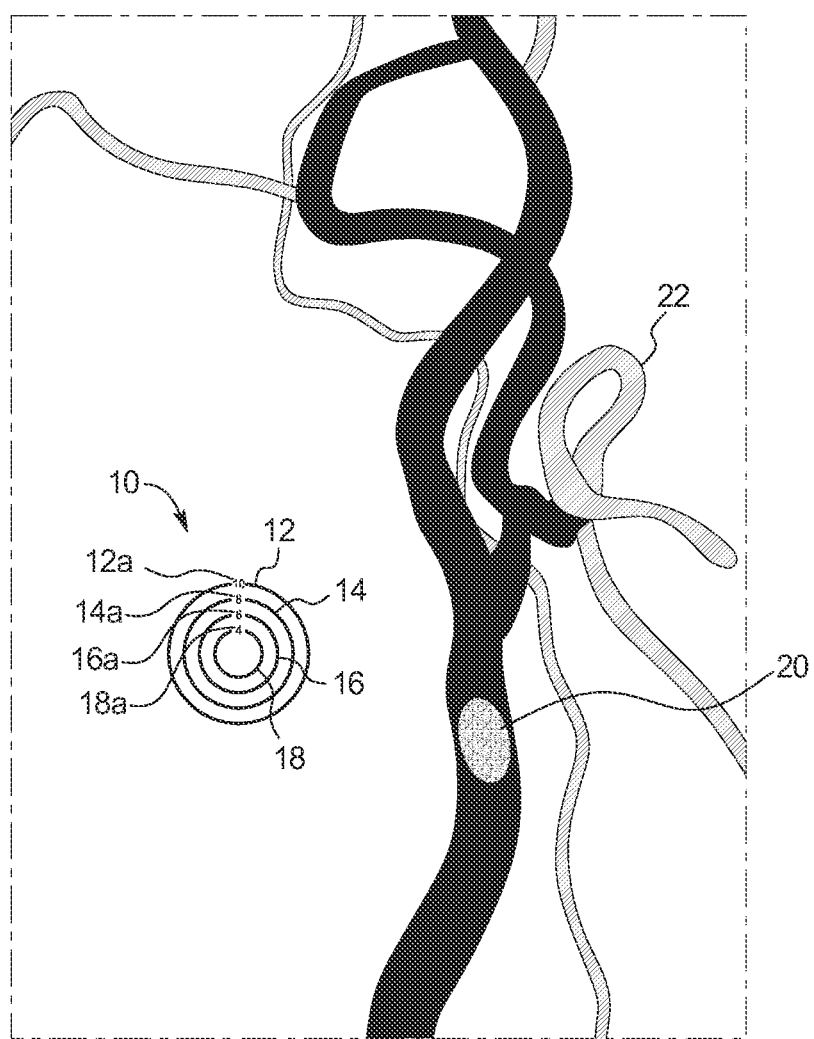
FIG. 2 illustrates a representation of a computer generated image of a blood vessel and of the medical device of FIG. 1 including the plurality of concentric circles of the marker.

FIG. 2 represents of a computer generated image of a blood vessel 22 (including clot 20) and marker 11. The image represented at FIG. 2 has been generated using an angiogram. Due to the radiopaque nature of circles 12, 14, 16 and 18 of marker 11, the circles are visible on the image.

To determine the size of a blood vessel, a user (e.g., a clinician) of medical device 10 first applies or places marker 11 onto a patient's skin near the patient's blood vessel (e.g., adheres marker 11 to the skin via an adhesive on the surface of marker 11). A machine, such as an X-ray machine, is then used to generate an image of the blood vessel and of the circles 12, 14, 16 and 18. That is, the radiation produced by the machine does not penetrate circles 12, 14, 16 and 18, but penetrates the remaining portion of marker 11 so as to produce an image of circles 12, 14, 16 and 18 along with blood vessel 22 and any clots (e.g., clot 20).

Referring further to FIG. 2 as an example, a clinician can compare the size of the imaged blood vessel 22 to the image of the circles 12, 14, 16 and 18 produced by the computer machine. With the plurality of concentric circles 12, 14, 16 and 18 of maker 11 appearing on the image, the user is able to quickly and accurately ascertain the size of the blood vessel regardless of which machine is used and the particular magnification of that machine.

In an embodiment, the clinician employs a mechanical instrument (e.g., calipers) to quickly measure the size of the imaged blood vessel. The user then places the mechanical instrument's measured size near the concentric circles. Viewing the symbols 12a, 14a, 16a, 18a (representing the diameters of concentric circles 12, 14, 16 and 18, respectively) against the measured size, the user is able to quickly ascertain the actual size of the blood vessel. It should be appreciated that any suitable mechanical instrument can be used to measure the imaged blood vessel and then compare the measured image blood vessel to the diameters of the concentric circles.

It should further be appreciated that the radiopaque concentric circles and the radiopaque symbols of the present disclosure can be made of any suitable material(s) that do not allow X-rays (or other suitable radiation used to generate an image of a blood vessel) to penetrate the circles. In one example, the radiopaque circles and/or symbols are made of gold or platinum. The remaining material of marker 11, (i.e., the material of marker 11 that does not include the material of the concentric circles and symbols) can be made of any suitable material for placing on the skin of the patient, which allows X-rays or any other suitable radiation to penetrate the material. In one example embodiment, the suitable material for marker 11 is plastic.

It should additionally be appreciated that the medical device marker of the present disclosure can include any suitable number of radiopaque concentric circles. For example, in various embodiments, the marker includes one, three or five radiopaque concentric circles instead of four as illustrated at FIG. 1. Similarly, it should be appreciated that the diameter of marker 11 and the diameters of each of the radiopaque concentric circles can be any suitable size that enables the blood vessel size to be accurately determined based upon the computer generated image of the vessel.

For example, in one embodiment, the diameters of the concentric circles range from about 2 mm to about 20 mm as measured from the inside to the outside of the marker. In another embodiment, the diameters of the circles are about 2 mm, 4 mm, 6 mm and 8 mm as measured from the inside to the outside of the marker. In yet another embodiment, the diameters of the circles are about 4 mm, 6 mm, 8 mm and 10 mm as measured from the inside to the outside of the marker. In still another embodiment, the diameters of the circles are about 14 mm, 16 mm, 18 mm and 20 mm as measured from the inside to the outside of the marker. It should also be appreciated that instead of the outside diameter of the marker being a radiolucent material (i.e., allowing X-rays or other suitable radiation to pass through the marker), the outside diameter of the marker could also include a radiopaque circle.

ASPECTS OF THE PRESENT DISCLOSURE

Aspects of the subject matter described herein may be useful alone or in combination with one or more other aspect described herein. Without limiting the foregoing description, in a first aspect of the present disclosure, a blood vessel sizing device includes a marker configured for placement on the skin of a patient, the marker defines a substantially circular shape and includes a plurality of radiopaque substantially concentric circles.

In accordance with a second aspect of the present disclosure, which can be used in combination with the first aspect or any one of aspects two to twenty, the blood vessel sizing device marker includes an adhesive for adhering the marker to the skin of the patient.

In accordance with a third aspect of the present disclosure, which can be used in combination with any one or more of the preceding aspects, the blood vessel sizing device marker includes a plurality of different radiopaque symbols, wherein each of the plurality of different radiopaque symbols represents a diameter of one of the plurality of substantially concentric circles.

In accordance with a fourth aspect of the present disclosure, which can be used in combination with any one or more of the preceding aspects, each of the radiopaque symbols is a geometric shape.

In accordance with a fifth aspect of the present disclosure, which can be used in combination with any one or more of the preceding aspects, each of the radiopaque symbols are numbers In accordance with a sixth aspect of the present disclosure, which can be used in combination with any one or more of the preceding aspects, each of the plurality of radiopaque substantially concentric circles has a diameter, the diameters ranging from about 2 mm to about 12 mm.

In accordance with a seventh aspect of the present disclosure, which can be used in combination with any one or more of the preceding aspects, each of the plurality of radiopaque substantially concentric circles includes at least three radiopaque substantially concentric circles.

In accordance with an eighth aspect of the present disclosure, which can be used in combination any one or more of the preceding aspects, the at least three radiopaque substantially concentric circles have diameters of about 6 mm, 8 mm, and 10 mm.

In accordance with a ninth aspect of the present disclosure, which can be used in combination with any one or more of the preceding aspects, the plurality of radiopaque substantially concentric circles includes at least four radiopaque substantially concentric circles.

In accordance with a tenth aspect of the present disclosure, which can be used in combination with the fifth aspect, the at least four substantially concentric circles have diameters of about 4 mm, 6 mm, 8 mm, and 10 mm.

In accordance with an eleventh aspect of the present disclosure, which can be used in combination with the fifth aspect, the at least four substantially concentric circles have diameters of about 14 mm, 16 mm, 18 mm, and 20 mm.

In accordance with a twelfth aspect of the present disclosure, which can be used in combination with any one or more of the preceding aspects, a blood vessel sizing device includes an adhesive marker configured for placement on the skin of a patient, wherein the marker defines a substantially circular shape and includes (i) a plurality of radiopaque substantially concentric circles and, and (ii) a plurality of different radiopaque symbols, wherein each of the plurality of different radiopaque symbols represents a diameter of one of the plurality of substantially concentric circles.

In accordance with a thirteenth aspect of the present disclosure, which can be used in combination with the twelfth aspect, the plurality of radiopaque symbols are at least one of (i) geometric shapes, and (ii) numbers.

In accordance with a fourteenth aspect of the present disclosure, which can be used in combination with any one or more of the preceding aspects, the diameters of the plurality of substantially concentric circles range from about 2 mm to about 20 mm.

In accordance with a fifteenth aspect of the present disclosure, which can be used in combination with any one or more of the preceding aspects, a blood vessel sizing method includes placing a marker having a plurality of radiopaque substantially concentric circles on the skin of a patient, imaging the blood vessel and the marker, and comparing the image of the blood vessel to the image of at least one of the plurality of radiopaque substantially concentric circles to determine a size of the blood vessel.

In accordance with a sixteenth aspect of the present disclosure, which can be used in combination with the fifteenth aspect, imaging the blood vessel and the marker includes using an angiogram.

In accordance with a seventeenth aspect of the present disclosure, which can be used in combination any one or more of the preceding aspects, comparing the imaged blood vessel to the imaged plurality of concentric circles to determine the size of the blood vessel includes measuring the imaged blood vessel and comparing the measured blood vessel to the imaged diameters of the plurality of radiopaque substantially concentric circles.

In accordance with an eighteenth aspect of the present disclosure, which can be used in combination any one or more of the preceding aspects, measuring the diameter of the imaged blood vessel includes using a mechanical instrument.

In accordance with a nineteenth aspect of the present disclosure, which can be used in combination any one or more of the preceding aspects, the marker includes a plurality of different radiopaque symbols, wherein each of the plurality of different radiopaque symbols represents a diameter of one of the plurality of substantially concentric circles.

In accordance with a twentieth aspect of the present disclosure, which can be used in combination any one or more of the preceding aspects, comparing the imaged blood vessel to the image of at least one of the plurality of concentric circles to determine the size of the blood vessel includes measuring the imaged blood vessel and comparing the measured blood vessel to the imaged diameters of the plurality of radiopaque substantially concentric circles and reading the symbols.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A blood vessel sizing device comprising:
a marker structure configured for placement on the skin of a patient, and further comprising:
a plurality of concentric circle shapes; and
a plurality of distinct geometric shape symbols,
wherein a selected concentric circle shape, from the plurality of circle shapes, has a first thickness in visible light between an inside diameter and an outside diameter, and the first thickness comprises a radiopaque material at the inside diameter and a radiolucent material at the outside diameter such that the selected concentric circle shape has a second thickness, less than the first thickness, when viewed in an X-ray image,
wherein a selected distinct geometric shape symbol, from the plurality of distinct geometric shape symbols, intersects the selected concentric circle shape, and
wherein the selected distinct geometric shape represents a diameter of the selected concentric circle shape that it intersects.

2. The blood vessel sizing device of claim 1, wherein the marker structure further comprises:
an adhesive for adhering the marker to the skin of the patient.

3. The blood vessel sizing device of claim 1, wherein the plurality of distinct geometric shape symbols comprise a triangle, a circle, a square and a pentagon.

4. The blood vessel sizing device of claim 1, wherein the plurality of distinct geometric shape symbols are numbers.

5. The blood vessel sizing device of claim 1, wherein the diameters of the plurality of concentric circle shapes range from about 2 mm to about 20 mm.

6. The blood vessel sizing device of claim 1, wherein there are at least four concentric circle shapes, which have diameters of about 4 mm, 6 mm, 8 mm, and 10 mm, respectively.

7. The blood vessel sizing device of claim 1, wherein there are at least four concentric circle shapes, which have diameters of about 14 mm, 16 mm, 18 mm, and 20 mm, respectively.

8. The blood vessel sizing device of claim 1, wherein the shape the marker structure defines is substantially circular.

9. A blood vessel sizing device comprising:
an adhesive marker structure configured for placement on the skin of a patient, the marker structure further comprising:
a plurality of substantially concentric circle shapes; and
a plurality of distinct geometric shape symbols,
wherein a selected concentric circle shape, from the plurality of substantially concentric circle shapes, has a first thickness in visible light between an inside diameter and an outside diameter, and the first thickness comprises a radiopaque material at the inside diameter and a radiolucent material at the outside diameter such that the selected concentric circle shape has a second thickness, less than the first thickness, when viewed in an X-ray image,
wherein a selected distinct geometric shape symbol, from the plurality of distinct geometric shape symbols, intersects the selected concentric circle shape, and
wherein the selected distinct geometric shape represents a diameter of the selected concentric circle shape that it intersects.

10. The blood vessel sizing device of claim 9, wherein the plurality of substantially concentric circle shapes comprises at least four substantially concentric circle shapes.

11. The blood vessel sizing device of claim 9, wherein the diameters of the plurality of substantially concentric circle shapes range from about 2 mm to about 20 mm.

12. The blood vessel sizing device of claim 9, wherein the shape the marker structure defines is substantially circular.

13. A blood vessel sizing method comprising:
placing a marker structure having a plurality of substantially concentric circle shapes on the skin of a patient, wherein a selected concentric circle shape, from the plurality of substantially concentric circle shapes, has a first thickness in visible light between an inside diameter and an outside diameter, and the first thickness comprises a radiopaque material at the inside diameter and a radiolucent material at the outside diameter;

imaging the blood vessel and the marker structure using X-ray radiation, wherein the selected concentric circle shape has a second thickness, less than the first thickness, when viewed in a resulting X-ray image;

measuring the imaged blood vessel using a mechanical calipers; and comparing, using the mechanical calipers, the measured blood vessel to the imaged diameters of the plurality of substantially concentric circle shapes.

14. The blood vessel sizing method of claim 13, wherein imaging the blood vessel and the marker structure includes using an angiogram.

15. The blood vessel sizing method of claim 13, wherein the marker structure includes a plurality of different radiopaque symbols, each of the plurality of different radiopaque symbols representing a diameter of one of the plurality of substantially concentric circle shapes.

16. The blood vessel sizing method of claim 15, wherein comparing, using the mechanical calipers, the imaged blood vessel to the imaged plurality of concentric circle shapes to determine the size of the blood vessel further comprises:
measuring the imaged blood vessel;
comparing the measured blood vessel to the imaged diameters of the plurality of radiopaque substantially concentric circle shapes; and
reading the symbols.

* * * * *